US00PP33514P3

(12) United States Plant Patent
Shipley et al.

(10) Patent No.: US PP33,514 P3
(45) Date of Patent: Sep. 28, 2021

(54) **PROSOPIS PLANT NAMED *DODONAEA VISCOSA* 'EMERALD ICE'**

(50) Latin Name: *Dodonaea viscosa*
Varietal Denomination: Emerald Ice

(71) Applicants: Nicholas Benoit Shipley, Tucson, AZ (US); Russ Allen Buhrow, Tucson, AZ (US)

(72) Inventors: Nicholas Benoit Shipley, Tucson, AZ (US); Russ Allen Buhrow, Tucson, AZ (US)

( * ) Notice: Subject to any disclaimer, the term of this patent is extended or adjusted under 35 U.S.C. 154(b) by 431 days.

(21) Appl. No.: 15/330,191

(22) Filed: Aug. 22, 2016

(65) Prior Publication Data

US 2018/0054936 P1 Feb. 22, 2018

(51) Int. Cl.
*A01H 5/12* (2018.01)
*A01H 5/02* (2018.01)
*A01H 6/00* (2018.01)

(52) U.S. Cl.
USPC ..... Plt./226
CPC ..... *A01H 5/02* (2013.01); *A01H 5/12* (2013.01); *A01H 6/00* (2018.05)

(58) Field of Classification Search
USPC ..... Plt./226
See application file for complete search history.

*Primary Examiner* — Anne Marie Grunberg

(57) ABSTRACT

A new and distinct *Dodonaea viscosa* plant named Emerald Ice is characterized by a broad, dense growth form, bright green oblanceolate leaves, no pollen production and freeze hardiness estimated to around 10° F.

7 Drawing Sheets

Latin name: *Dodonaea viscosa.*
Varietal denomination: Emerald Ice.

BACKGROUND OF THE INVENTION

*Dodonaea viscosa*, commonly called hopbush, is a large shrub or small tree of the plant family Sapindaceae native to tropical, subtropical and warm temperate regions worldwide. The species is quite variable in color, form and cold hardiness, with many unpatented cultivars used as landscape plants which can be grown as medium-large shrubs, small trees, hedges, screens and for erosion control and revegetation plantings. Hopbush is noted for being tolerant of poor soils, heat and drought. Many of the currently cultivated forms have limited cold hardiness, often listed as around 15° F. but are frequently severely frost damaged or killed to the ground in the low to mid 20's.

The present invention relates to a new and distinct cultivar of *Dodonaea*. The cultivar originated as a cutting from an undamaged chance seedling plant discovered growing in a cultivated residential area near Nogales, Ariz. following a severe freeze in the winter of 2012. The source of the seed from which the plant was produced is unknown, but other *Dodonaea* plants were growing in the vicinity. Other nearby plants were similar in appearance but damaged by the freeze. The minimum temperature of that freeze at that location was estimated to be between 5 and 10° F.

The plant was found to be especially cold hardy with excellent growth form and is the object of this application.

SUMMARY OF THE INVENTION

Among the features that distinguish the new *Dodonaea* cultivar from all other available and commercial varieties of *Dodonaea* known to the inventors are the following combination of characteristics: plants female, without stamens, leaves oblanceolate, color 137A/137B (adaxial/abaxial), plant form broad and dense, with excellent freeze hardiness relative to other available cultivars.

The propagation procedure was as follows: Semihardwood cuttings were prepared by cutting to 3" in length, then placed into a rooting solution of DIP'N GRO™ at a ratio of 1:10 with water. Cuts were placed in trays containing ground coconut hulls, then moved to a rooting greenhouse near Sahuarita, Ariz. with temperature ranging from 65-85° F. and 85-90% relative humidity. Humidity is controlled with a fogging system and temperature with evaporative cooling. Rooting was completed within 6 weeks.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Dodonaea viscosa* 'Emerald Ice' growing near Tucson, Ariz., depicted in color as nearly correct as is possible to make in a color illustration of the character.

DETAILED PLANT DESRIPTION

Figure 1:
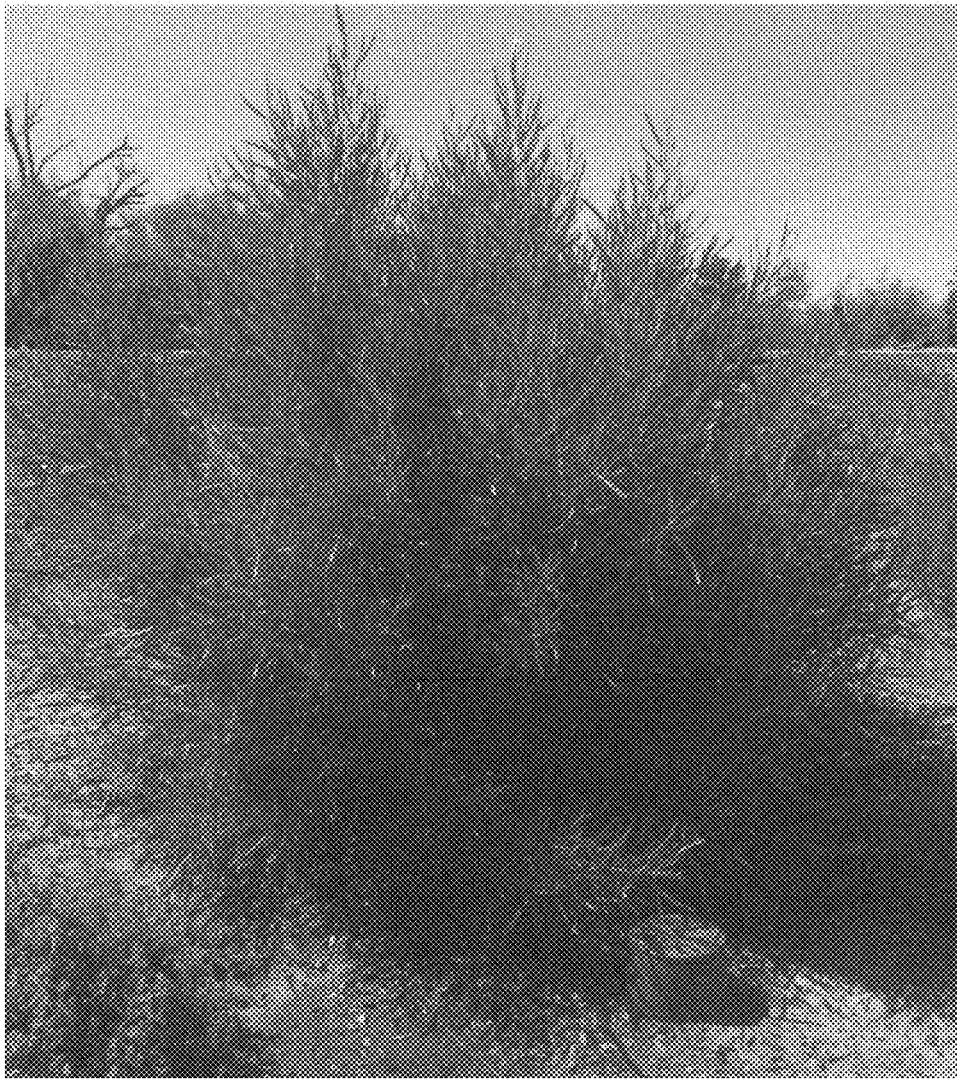
FIG. 1 shows an example of *Dodonaea viscosa* 'Emerald Ice' at 3 years from cutting growing near Tucson, Ariz.
Figure 2:
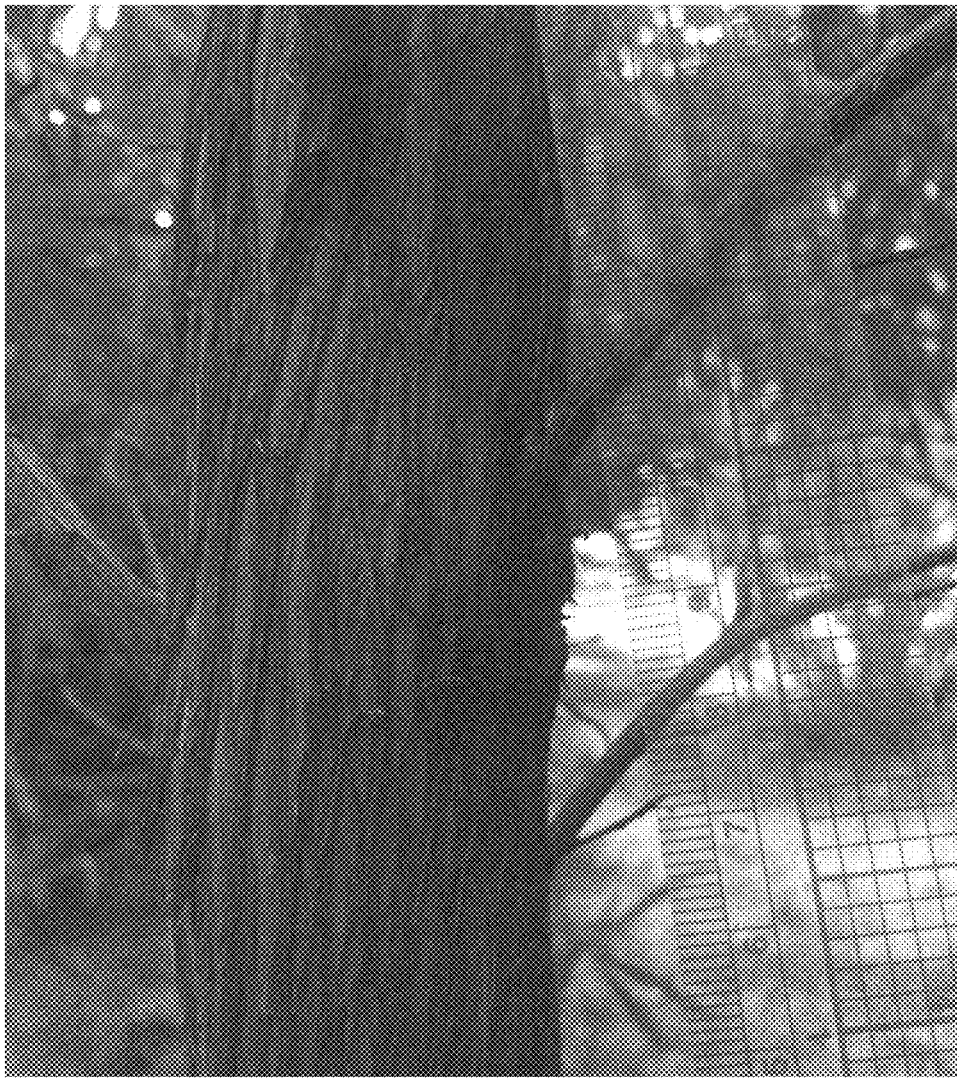
FIG. 2 shows a trunk of *Dodonaea viscosa* 'Emerald Ice' at 3 years from cutting growing near Tucson, Ariz.
Figure 3:
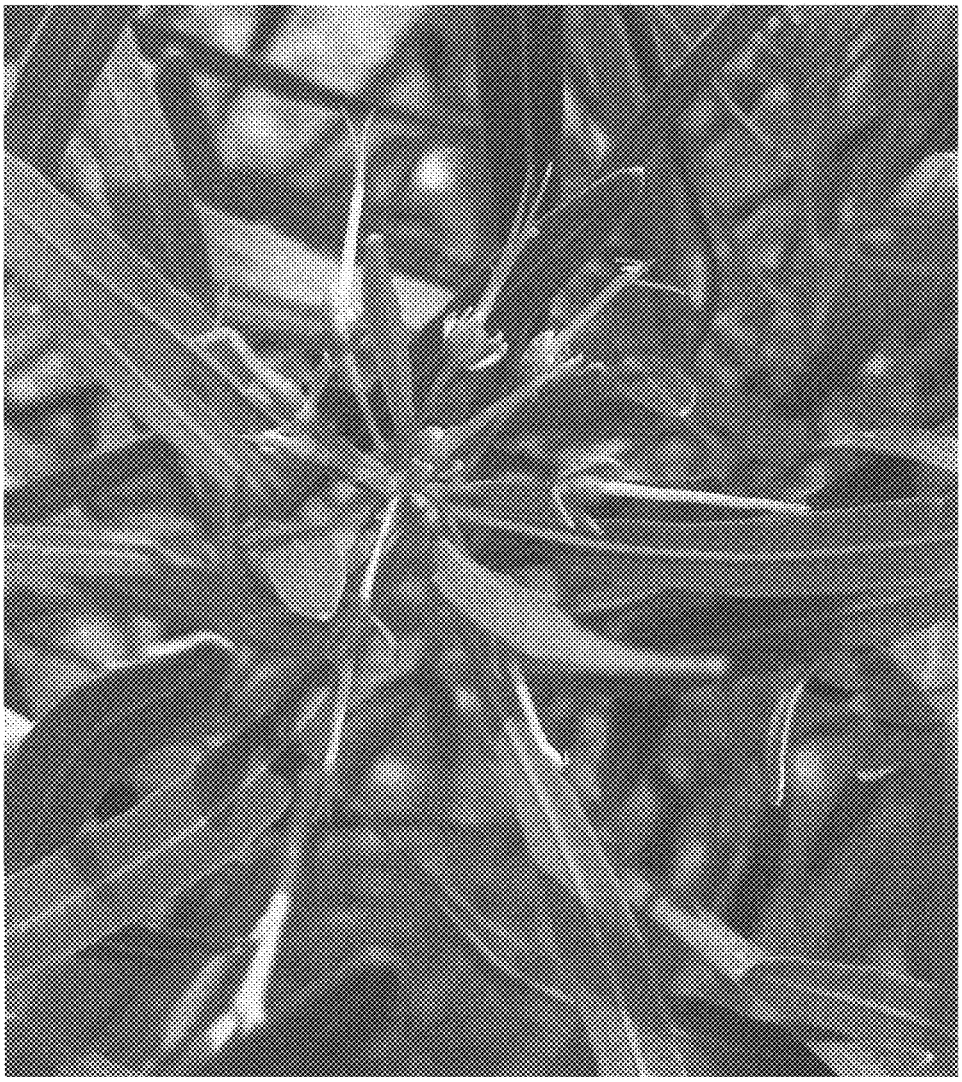
FIG. 3 shows the foliage and inflorescence of *Dodonaea viscosa* 'Emerald Ice' at the time of flower opening.
Figure 4:
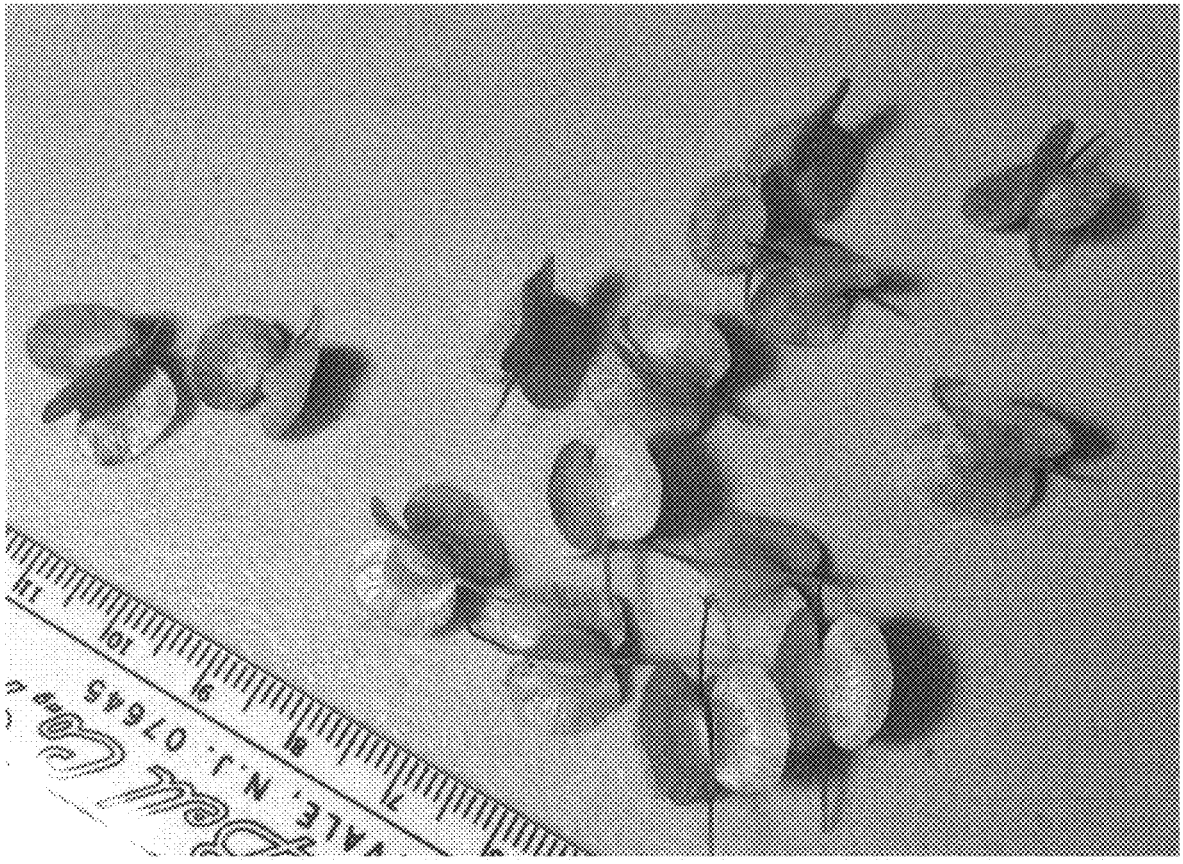
FIG. 4 shows mature fruits of *Dodonaea viscosa* 'Emerald Ice'.
Figure 5:
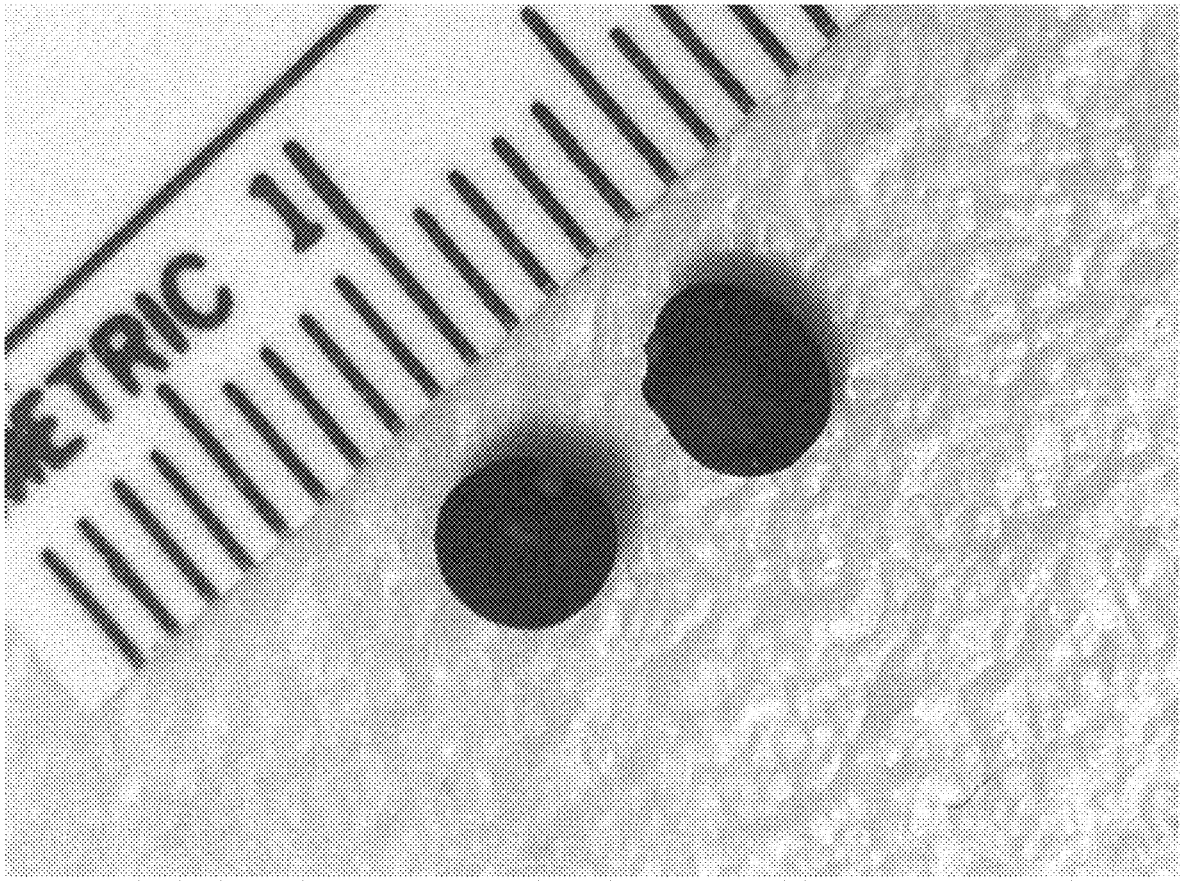
FIG. 5 shows seeds of *Dodonaea viscosa* 'Emerald Ice'.
Figure 6:
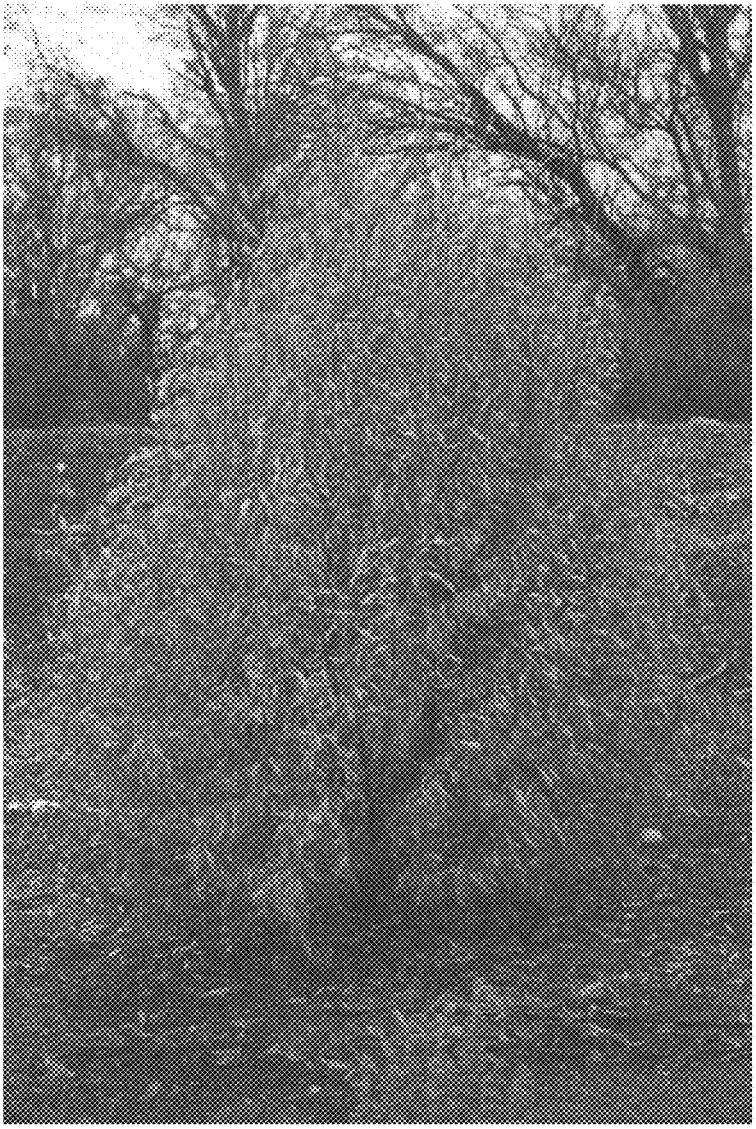
FIG. 6 shows an example of a non-hardy form of hopbush severely damaged following a freeze of approximately 18-20° F. The adjacent 'Emerald Ice' plant was undamaged.
Figure 7:
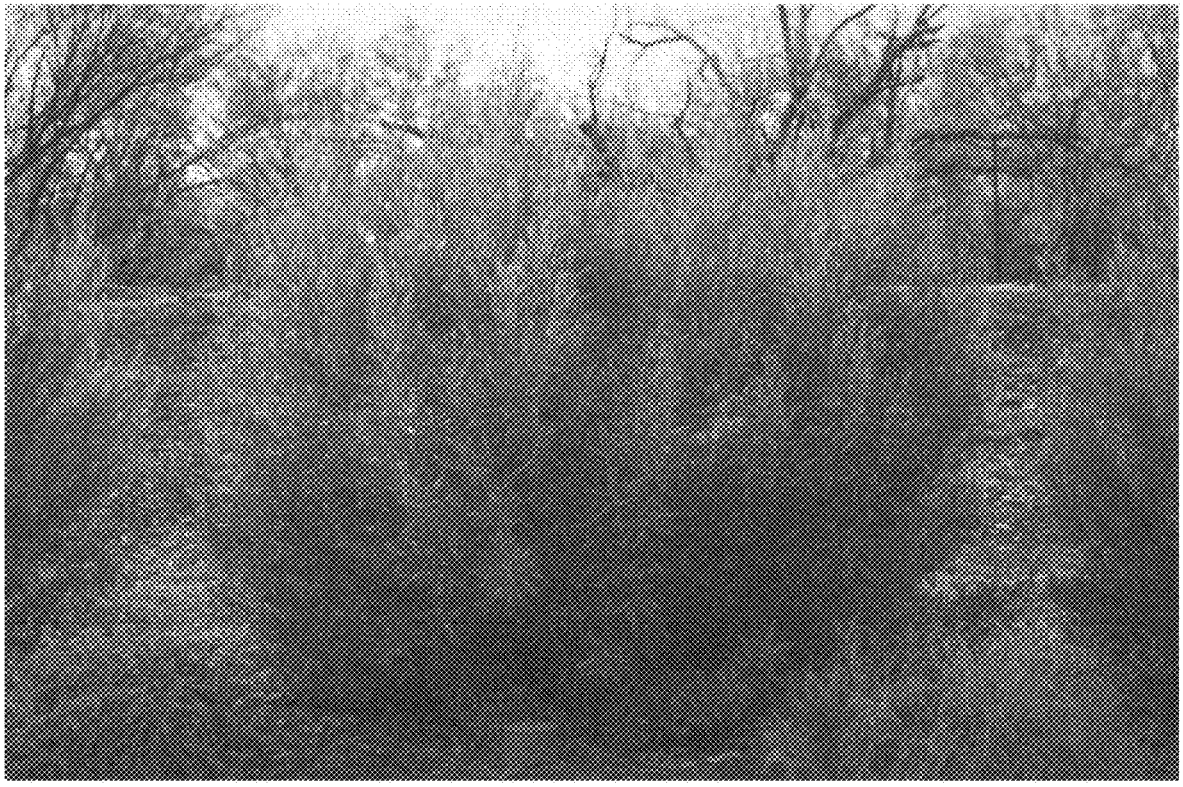
FIG. 7 shows the undamaged 'Emerald Ice' plant growing adjacent to the plant shown in FIG. 6.

The following is a detailed description of the new *Dodonaea* plant is based upon measurements taken from a plant about 3 years old from a cutting growing near Tucson, Ariz. The color descriptions are based upon the 5$^{th}$ edition R.H.S. Colour Chart. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Overall plant: Shrubby, dense, about 9 feet tall×9 feet wide.

Trunks and mature branches: Up to 3 inches thick, bark shredding, fibrous, and somewhat ropelike. Color varies from 168D to 200B from the youngest to the oldest portions of the bark.

Branch angle: 30-50 degrees.

Branches: Slightly zigzagged at the nodes, internode length ranges from 4-48 mm in length.

Young stems 1.5×2 mm in diameter, somewhat angular, with a rib extending downward from the leaf base, glabrous, viscid, color 144B. By the time the stems reach about 2 mm in diameter the stem becomes essentially terete. By the time the stem reaches 2-2.5 mm in diameter color grades to 152B and with further maturity color 167B. At stem diameter 2.5-4 mm growth produces cracks in the epidermis, the cracked areas display color 152B, the original surface remaining color 167B. Stems by 10 mm diameter have bark much like the larger stems and trunk.

Leaves: Evergreen, sessile, oblanceolate, upcurved laterally, measuring from 3.5-7.5 mm wide×48-90 mm long; midrib raised on both surfaces; veins obscure, pinnate, slightly visible on adaxial side. Barely visible glandular hairs sparsely present on the basal portion of the midrib and along the leaf margin.

Leaf surface: Adaxially and abaxially similar, glabrous, viscid, adaxially color 137A, abaxially 137B.

Inflorescence: An axillary, reduced, cymose panicle of 3-15 female flowers. Inflorescence in bud 9 mm long×8 mm wide, covered loosely with chaotically spreading glandular hairs +−0.25 mm long. Most of these hairs become deciduous with inflorescence maturity. Inflorescence color at this stage is 139C.

Peduncle: Peduncle bract 3 mm long×1 mm wide, lance-linear, somewhat succulent and viscid with scattered glandular hairs, denser at the base; color 139C; peduncle in bud 1.5 mm long×0.8 mm diameter, terete, color 139C. Peduncle at maturity is 1.5-3 mm long×0.3-0.5 mm diameter, terete, resinous with scattered glandular hairs, color 146D.

Pedicel: Pedicel bract 1-1.5 mm long×0.3-0.5 mm wide, lanceolate, with scattered glandular hairs denser at the base, viscid, color 139C; pedicels in bud 1.5-3 mm long×0.3 mm with scattered glandular hairs, densest at the base, viscid, color 139C. Pedicels at anthesis are 6-10 mm long×0.5 mm in diameter. Pedicels at fruit maturity 6-11 mm long×0.3 mm diameter basally to 1 mm at the apex, terete, resinous, verrucate, tapering thicker to an abscission layer 1 mm below the base of the fruit, color 146D. A second abscission layer is present at the attachment to the peduncle.

Buds: 2.5 mm long×1.1 mm thick, ovoid/ellipsoid with scattered, basally glandular hairs about 0.5 mm long. Buds constricted longitudinally along the sepal margins, bud color 139C. During bud development the style and stigma elongate rapidly such that by the time of flower opening they project considerably past the tip of the unopened buds.

Flowers: Pistillate, lacking both stamens and petals.

Calyx: Typically comprised of 4 sepals, but varying from 3-5. Sepals are 2.5-3 mm long×1-1.5 mm wide, lanceolate, more or less carinate. Sepal adaxial surface glabrous, viscid, color 144C, abaxial surface with scattered hirsutulous hairs, viscid, color N144A.

Staminal whorl: Represented by vestigial bumps/appendages 8-10 in number centered on and alternating with the sepal bases, these bumps ovoid, about 0.3 mm long×0.015 mm wide, color 144C.

Pistil: 8-14 mm long.

Ovary: Short stipitate, the stipe 0.5 mm long×0.5 mm thick, stipe color 144C. Ovary rounded, trianguloid or squarish, depending upon number of locules, 1.5 mm long×1.5 mm thick. Ovary color is 144A. Ovary viscid, with scattered hirsutulous hairs.

Style with stigmas: 9-11 mm long×0.5 mm thick, grooved, the grooves aligned with the gaps between the stigma lobes. Stigma has 4 lobes, each about 2 mm long×0.25 mm thick, pointed and spreading. Style and stigma color 153A.

Fruit at maturity: Generally spheroidal in outline, a 2-4 celled, winged, septicidal capsule containing up to 2 seeds/locule, but typically aborting to 1-2 seeds/fruit. The seeds often remain loosely attached to the associated winged fruit segment at dehiscence and are wind dispersed as such. Wings are attached at the locules longitudinally and radiate outward 2.5-3.5 mm from the fruit surface. Overall fruit size is 11-12 mm long×10-13 mm wide and thick. Fruit surface is reticulate, lustrous and not viscid. The wings are like the rest of the fruit, except the reticulum is radiate. Base color 145D, Reticulum color 145D. Fruits exposed to the sun have a base color of 145D, the reticulum 185B. Fruits dry close to 165C.

Seeds: Ovoid, laterally compressed, slightly lustrous, somewhat skewed to the side in length, color 187A. Using the hilum as the starting point, 3-3.5 mm long×2.5-3.5 mm wide×1.5 thick. The hilum is somewhat raised, round, and 0.5 mm in diameter, color 166A.

COMPARISONS TO RELATED *DODONAEA*

Cultivated *Dodoneas* are found throughout the warmer parts of the world and quite variable in form, color, hardiness, and leaf shape. To the authors' knowledge, none of these forms are patented. Most of the forms in the American nursery trade are either seed grown and quite variable or the reddish-purple cultivar 'Purpurea' which originated in New Zealand. Compared to 'Purpurea', 'Emerald Ice' has superior freeze hardiness and a very different leaf color. 'Emerald Ice' also is broader and denser than 'Purpurea' in growth form.

We claim:

1. A new and distinct *Dodonaea* plant substantially as described and illustrated herein.

* * * * *